United States Patent [19]

Tucker

[11] 4,182,911

[45] Jan. 8, 1980

[54] OPTICALLY-ACTIVE 1-ARYLOXY-2-PROPANOL INTERMEDIATES OF (S)-ABSOLUTE CONFIGURATION

[75] Inventor: Howard Tucker, Macclesfield, England

[73] Assignee: Imperial Chemical Industries Limited, London, England

[21] Appl. No.: 862,517

[22] Filed: Dec. 20, 1977

Related U.S. Application Data

[62] Division of Ser. No. 694,323, Jun. 9, 1976, Pat. No. 4,085,136, Division of Ser. No. 520,845, Nov. 4, 1974, abandoned.

[30] Foreign Application Priority Data

Nov. 9, 1973 [GB] United Kingdom ............... 52077/73

[51] Int. Cl.$^2$ ............................................. C07C 43/20
[52] U.S. Cl. ..................................... 568/633; 568/583; 568/584; 568/586; 568/587; 568/636; 568/637; 568/638; 568/643; 568/644; 568/645; 568/646; 568/648; 568/649; 568/650; 568/654
[58] Field of Search ................... 260/613 R; 568/583, 568/584, 586, 587, 633, 636, 637, 638, 643, 644, 645, 646, 648, 649, 650, 654

[56] References Cited

U.S. PATENT DOCUMENTS

| 2,738,351 | 3/1956 | Dickison et al. | 260/293.83 |
| 3,494,939 | 2/1970 | Smith | 260/348 |
| 3,686,320 | 8/1972 | Fitzmaurice et al. | 260/613 R |

FOREIGN PATENT DOCUMENTS

| 1251716 | 10/1971 | United Kingdom. |
| 1252399 | 11/1971 | United Kingdom. |
| 1410513 | 10/1975 | United Kingdom. |

OTHER PUBLICATIONS

Sh. Mamedov et al., "Ethers of glycols and their derivatives" in Chem. Abs., vol. 60, May. 1964, 13172g.
Danilewicz et al., J. Med. Chem., 1973, vol. 16, No. 2, pp. 168, 169.
Balfe et al., "The Dependence of Optical Rotary Power" in J. Chem. Soc. 1950, pp. 1861–1866.

*Primary Examiner*—Arthur P. Demers
*Attorney, Agent, or Firm*—Cushman, Darby & Cushman

[57] ABSTRACT

Novel optically-active (S)- 1-aryloxy-2,3-epoxy-propane derivatives, a process for their manufacture, various intermediates used in the preparation thereof, and a process for using them for the manufacture of optically-active (S)-1-aryloxy-3-amino-2-propanol derivatives useful as β-adrenergic blocking agents.

6 Claims, No Drawings

OPTICALLY-ACTIVE 1-ARYLOXY-2-PROPANOL INTERMEDIATES OF (S)-ABSOLUTE CONFIGURATION

This is a division of application Ser. No. 694,323, filed June 9, 1976, now U.S. Pat. No. 4,085,136, as a division of Ser. No. 520,845, filed Nov. 4, 1974, now abandoned.

This invention relates to new chemical intermediates useful for the preparation of therapeutically-active compounds.

It is known, from the Journal of Medicinal Chemistry, 1973, Volume 16, pages 168–169, that an optically-active 1-aryloxy-2,3-epoxypropane derivative may be prepared which may be reacted with an amine such as isopropylamine to give an optically-active 1-aryloxy-3-amino-2-propanol derivative. However, the epoxy derivative thus described is a laevorotatory compound having the (R)— absolute configuration and the 1-aryloxy-3-amino-2-propanol derivative obtained therefrom is a dextrorotatory compound also having the (R)— absolute configuration. It is well known that many 1-aryloxy-3-amino-2-propanol derivatives possess valuable $\beta$-adrenergic blocking activity and are therefore useful in the treatment of, inter alia, heart diseases, and it is further known that if a racemic such compound is resolved into its optically-active enantiomorphs, the $\beta$-adrenergic blocking activity usually predominates in the laevorotatory isomer having the (S)— absolute configuration.

We have now devised, and herein lies our invention, a means of obtaining 1-aryloxy-2,3-epoxypropane derivatives having the (S)— absolute configuration which may be used as intermediates in the manufacture of 1-aryloxy-3-amino-2-propanol derivatives which possess $\beta$-adrenergic blocking activity.

According to the invention there is provided an optically-active epoxide having the (S)— absolute configuration and having the formula:

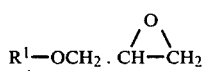

wherein $R^1$ stands for an aryl radical which may optionally bear one or more substituents.

According to a further feature of the invention there is provided a process for the manufacture of the epoxide of the invention which comprises treating an optically-active compound having the (R)— absolute configuration of the formula:
$R^1$—OCH$_2$.CHOH.CH$_2$Z wherein $R^1$ has the meaning stated above and wherein Z stands for a displaceable radical, with a base.

A suitable value for Z is, for example, a halogeno radical, for example the chloro, bromo or iodo radical, or a sulphonyloxy radical, for example an alkanesulphonyloxy radical of up to 6 carbon atoms, for example the methanesulphonyloxy radical, or an arenesulphonyloxy radical of up to 10 carbon atoms, for example the toluene-p-sulphonyloxy radical.

A suitable base is, for example, an alcoholic or aqueous alcoholic solution of an alkali metal hydroxide, for example sodium hydroxide.

The last-mentioned compound may be obtained by conventional means from an optically-active diol having the (S)— absolute configuration of the formula:

wherein $R^1$ has the meaning stated above, which in turn may be obtained by removal of the protecting group Y from an optically-active compound having the (S)—absolute configuration of the formula:

wherein $R^1$ has the meaning stated above and wherein Y stands for an easily-removable protecting group.

A suitable value for Y is, for example, an $\alpha$-arylalkyl or $\alpha$-arylalkoxycarbonyl radical, for example the benzyl or benzyloxycarbonyl radical, which may easily be removed by hydrogenolysis, or a tertiary-alkyl or tertiary-alkoxycarbonyl radical, for example the t-butyl or t-butoxycarbonyl radical, which may easily be removed by treatment with anhydrous acid.

The last-mentioned compound may be obtained by the reaction of an optically-active compound having the (S)— absolute configuration of the formula:

wherein Y and Z have the meanings stated above, with a phenol of the formula $R^1$—OH, wherein $R^1$ has the meaning stated above. The compound of the last mentioned formula wherein Z is toluene-p-sulphonyloxy and Y is benzyl is a known compound, and other compounds of this type may be obtained by analogous means from the known (S)-2,3-O-isopropylideneglycerol (obtainable from D-mannitol) by protection of the 1-primary-hydroxy radical with the protecting group Y, removal of the isopropylidene protecting group and conversion of the 3-primary-hydroxy radical to the displaceable radical Z.

The following optically-active intermediate compounds which have the formulae:

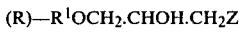

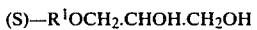

wherein $R^1$, Y and Z have the meanings stated above are all novel compounds and these form further features of the invention.

When the aryl radical $R^1$ bears a substituent labile to hydrogenolysis conditions, for example an iodo, cyano or nitro radical, or a radical containing an olefinic group or a thio group, Y is preferably a tertiary-alkyl-containing protecting group.

A suitable value for $R^1$ is, for example, a phenyl radical which is unsubstituted or which bears one, two or three substituents selected from halogeno radicals, for example fluoro, chloro, bromo or iodo radicals; hydroxy, amino, hydroxyiminomethyl, nitro and cyano radicals; alkyl, cycloalkyl, alkenyl, alkynyl, alkoxy, cycloalkoxy, alkenyloxy, alkynyloxy, alkylamino and alkylthio radicals each of up to 6 carbon atoms, for example methyl, ethyl, n-propyl, isopropyl, t-butyl, cyclopropyl, cyclopentyl, allyl, ethynyl, methoxy, ethoxy, isopropoxy, n-butoxy, cyclopentyloxy, allyloxy, propargyloxy, methylamino, methylthio and ethylthio radicals; aryl, aryloxy, arylamino, arylthio, arylsulphonyl, aralkyl and aralkoxy radicals each of up to 10 carbon atoms, for example phenyl, phenoxy, p-tolyloxy, anilino, phenylthio, phenylsulphonyl, benzyl and benzyloxy radicals; acyl and acyloxy radicals each of up to 10 carbon atoms, for example formyl, acetyl, propionyl, phenylacetyl, β-phenylpropionyl, benzoyl and acetoxy radicals; hydroxyalkyl, hydroxyalkenyl, hydroxyalkoxy, aminoalkyl, cyanoalkyl, cyanoalkenyl and cyanoalkoxy radicals each of up to 6 carbon atoms, for example hydroxymethyl, β-hydroxyethyl, 3-hydroxyprop-1-enyl, β-hydroxyethoxy, aminomethyl, cyanomethyl, cyanoethyl, β-cyanovinyl and γ-cyanopropoxy radicals; alkoxyalkyl, alkoxyalkoxy and (oxacycloalkyl)alkoxy radicals each of up to 10 carbon atoms, for example methoxyethyl, methoxyethoxy, ethoxyethoxy, tetrahydrofuran-2-ylmethoxy and tetrahydropyran-2-ylmethoxy radicals; and radicals of the formula:

$R^2R^3N-CO-A-$, $R^2R^3N-CO-A^1-O-$, $R^3CO-NR^2-A-$, $R^3SO_2-NR^2-$ and $R^3NH-CO-NH-A-$ wherein A stands for a direct link, or for an alkylene radical of 1 to 6 carbon atoms, for example the methylene, ethylene, trimethylene or 1-methylethylene radical, or for an alkenylene radical of 2 to 6 carbon atoms, for example the vinylene radical; wherein $A^1$ stands for an alkylene radical as defined above for A; wherein $R^2$ stands for hydrogen or for an alkyl radical of up to 6 carbon atoms, for example the methyl radical; and wherein $R^3$ stands for hydrogen, or for an alkenyl, cycloalkyl, hydroxyalkyl or alkoxyalkyl radical each of up to 6 carbon atoms, for example the allyl, cyclopropyl, cyclopentyl, cyclohexyl, β-hydroxyethyl, γ-hydroxypropyl, 2-hydroxy-1-methylethyl, 2-hydroxy-1,1-dimethylethyl or β-methoxyethyl radical, or for an alkyl, aryl, aralkyl or aralkenyl radical each of up to 10 carbon atoms, for example the methyl, ethyl, n-propyl, isopropyl, n-butyl, t-butyl, n-pentyl, n-hexyl, n-nonyl, phenyl, p-tolyl, p-chlorophenyl, benzyl or styryl radical.

Alternatively, $R^1$ may be a bi- or poly-cyclic aromatic radical wherein at least one ring, to which the side-chain is attached, is a benzene ring. Such a radical $R^1$ may be, for example, a naphthyl, 5,8-dihydronaphthyl, 5,6,7,8-tetrahydronaphthyl, 5,8-ethano-5,6,7,8-tetrahydronaphthyl, indanyl, indenyl, fluorenyl, anthryl, chromanyl, chromenyl, thiochromanyl, benzodioxanyl, quinolinyl, tetrahydroquinolinyl, benzofuranyl, dihydrobenzofuranyl, benzothienyl, indolyl or indolinyl radical, which may optionally be substituted as stated above for the phenyl radical $R^1$, and which may also, where there is an appropriate degree of partial saturation, optionally bear an oxo substituent.

Alternatively, $R^1$ may be a monocyclic heterocyclic radical, for example the thiazoyl or thiadiazolyl radical, which may be appropriately substituted.

A preferred value for $R^1$, preferred because a 1-aryloxy-3-amino-2-propanol derivative bearing such a 1-aryloxy group has been extensively studied as a β-adrenergic blocking agent, is the 2-tolyl, 3-tolyl, 2,3-dimethylphenyl, 2-chloro-5-methylphenyl, 2-allylphenyl, 2-allyloxyphenyl, 2-cyclopropylphenyl, 2-cyclopentylphenyl, 2-cyanophenyl, 2-methoxyphenyl, 2-methylthiophenyl, 2-(tetrahydrofuran-2-yl)-methoxyphenyl, 4-acetamidophenyl, 4-carbamoylmethylphenyl, 2-(N-methylcarbamoylmethoxy)phenyl, 2-(N-β-hydroxyethylcarbamoylmethoxy)phenyl, 2-acetyl-4-butyramidophenyl, 4-(3-cyclohexylureido)phenyl, 1-naphthyl, 5,8-dihydro-1-naphthyl, 5,6,7,8-tetrahydro-5-oxo-1-naphthyl, 5,8-ethano-5,6,7,8-tetrahydro-1-naphthyl, 4-indanyl, 7-indenyl, 4-indolyl, 5-methyl-8-coumarinyl, 8-thiochromanyl or 4-morpholino-1,2,5-thiadiazol-3-yl radical.

According to a further feature of the invention there is provided a process for the manufacture of an alkanolamine derivative having the (S)— absolute configuration and having the formula:

$R^1OCH_2.CHOH.CH_2NHR^4$ wherein $R^1$ has the meaning stated above and wherein $R^4$ stands for an alkyl, hydroxyalkyl or cycloalkyl radical each of up to 6 carbon atoms, for example the isopropyl, s-butyl, t-butyl, 2-hydroxy-1,1-dimethylethyl or cyclopentyl radical, which comprises the reaction of the optically-active epoxide of the invention with an amine of the formula $R^4NH_2$, wherein $R^4$ has the meaning stated above.

The last-mentioned process may be carried out by by conventional means.

The invention is illustrated but not limited by the following Examples:

EXAMPLE 1 p-Carbamoylmethylphenol (4.5 g.) is added to a solution of sodium (0.7 g.) in methoxyethanol (15 ml.) and the mixture is stirred for 15 minutes. A solution of (+)-3-benzyloxy-1-toluene-p-sulphonyloxypropan-2-ol (10 g.) is methoxyethanol (25 ml.) is added and the mixture is heated under reflux for 1.5 hours, cooled and poured into ice-cold water. The mixture is filtered and the solid residue is crystallised from ethyl acetate. There is thus obtained 5.5 g. of (+)-3-benzyloxy-1-p-carbamoylmethylphenoxypropan-2-ol, m.p. 132°–133° C., $[\alpha]_D^{21} +7.4°$ (c, 1% in methanol).

EXAMPLE 2

A solution of (+)-3-benzyloxy-1-p-carbamoylmethylphenoxypropan-2-ol (5.5 g.) in methanol (150 ml.) is shaken in an atmosphere of hydrogen at atmospheric pressure in the presence of a 30% palladium-on-carbon catalyst until the required amount of hydrogen has been absorbed. The mixture is filtered and the filtrate is evaporated to dryness. The solid residue is crystallised from methanol and there is thus obtained (+)-1-p-carbamoylmethylphenoxypropane-2,3-diol, m.p. 182.5°–184° C., $[\alpha]_D^{21} +7.4°$ (c, 0.5% in methanol).

EXAMPLE 3

Toluene-p-sulphonylchloride (2.8 g.) is added to a cooled solution of (+)-1-p-carbamoylmethylphenoxypropane-2,3-diol (3.3 g.) in pyridine (33 ml.) and the mixture is allowed to stand for 20 hours at +4° C. The mixture is diluted with ethyl acetate (25 ml.) and poured into ice-cold aqueous sulphuric acid (12.8 ml. of concentrated sulphuric acid in 78 ml. of water). The organic layer is separated and the acidic aqueous layer is extracted three times with ethyl acetate (25 ml. each time). The combined ethyl acetate solutions are dried over anhydrous magnesium sulphate and evaporated to dryness and the residual oil is triturated with ether. The solid thus obtained is crystallised from ethyl acetate and there is thus obtained 1.35 g. of (−)-1-p-carbamoylmethylphenoxy-3-toluene-p-sulphonyloxypropan-2-ol, $[\alpha]_D^{21}$ −7.4° (c, 0.5% in methanol).

EXAMPLE 4

A solution of (−)-1-p-carbamoylmethylphenoxy-3-toluene-p-sulphonyloxypropan-2-ol (1.25 g.) in 20% aqueous sodium hydroxide solution is stirred at laboratory temperature for 15 minutes. Water (25 ml.) is added and the mixture is filtered. The solid residue is crystallised from ethyl acetate and there is thus obtained (+)-1-p-carbamoylmethylphenoxy-2,3-epoxypropane, m.p. 147°–149° C., $[\alpha]_D^{21}$ +4.8° (c, 1% in methanol).

EXAMPLE 5

A mixture of (+)-1-p-carbamoylmethylphenoxy-2,3-epoxypropane (0.5 g.), isopropylamine (5 ml.) and isopropanol (5 ml.) is heated under reflux for 1.5 hours and is then evaporated to dryness. The residue is crystallised from ethyl acetate and there is thus obtained (−)-1-p-carbamoylmethylphenoxy-3-isopropylaminopropan-2-ol, m.p. 151.5°–153° C., $[\alpha]_D^{21}$ −13.6° (c, 1% in aqueous N-hydrochloric acid).

EXAMPLE 6

The process described in Example 1 is repeated except that the appropriate phenol is used as starting material in place of p-carbamoylmethylphenol. There are thus obtained the compounds described in the following table:

| | $R^1$—OCH$_2$ . CHOH . CH$_2$OCH$_2$C$_6$H$_5$ | |
|---|---|---|
| $R^1$ | $[\alpha]_D^{21}$ | c (% in methanol) |
| 1-naphthyl- | + 7.7° | 0.65 |
| p-acetamidophenyl- | + 1.68° | 5.2 |
| o-(N-methylcarbamoylmethoxyphenyl)- | + 6.2° | 2.2 |
| 4-indanyl- | − 3.0° | 1.0 |
| m-tolyl | + 2.5° | 5.0 |

EXAMPLE 7

The process described in Example 2 is repeated except that the compounds described in Example 6 are used as starting materials. There are thus obtained the compounds described in the following table:

| | $R^1$—OCH$_2$ . CHOH . CH$_2$OH | | |
|---|---|---|---|
| $R^1$ | M.p.(°C.) | $[\alpha]_D^{21}$ | c (% in methanol) |
| 1-naphthyl- | 108–109 | + 10.2° | 1.0 |
| p-acetamidophenyl- | 146–150 | + 5.01° | 1.0 |
| o-(N-methylcarbamoyl-methoxyphenyl)- | 97–100 | + 12.6° | 1.0 |
| 4-indanyl- | 95–96 | + 3.2° | 1.0 |
| m-tolyl- | 50–52 | + 8.0° | 1.0 |

EXAMPLE 8

The process described in Example 3 is repeated except that the diols described in Example 7 are used as starting materials. There are thus obtained the toluene-p-sulphonyl derivatives described in the following table:

| | $R^1$—OCH$_2$ . CHOH . CH$_2$OSO$_2$C$_7$H$_8$ | |
|---|---|---|
| $R^1$ | $[\alpha]_D^{21}$ | c (% in methanol) |
| 1-naphthyl- | − 17.3° | 1.4 |
| p-acetamidophenyl- m.p. 118°–119° C.) | − 9.9° | 1.0 |
| o-(N-methylcarbamoylmethoxyphenyl)- | + 5.0° | 1.0 |
| 4-indanyl- | − 6.95° | 2.0 |
| m-tolyl- | − 6.0° | 1.0 |

EXAMPLE 9

The process described in Example 4 is repeated except that the compounds described in Example 8 are used as starting materials. There are thus obtained the epoxy-compounds described in the following table:

$$R^1-OCH_2 . CH\overset{O}{\overset{\diagup\diagdown}{\text{———}}}CH_2$$

| $R^1$ | M.p.(°C.) | $[\alpha]_D^{21}$ | c (% in methanol) |
|---|---|---|---|
| 1-naphthyl- | (oil) | + 31.4° | 1.5 |
| p-acetamidophenyl- | 104–107 | + 10.0° | 1.0 |
| o-(N-methylcarbamoyl-methoxyphenyl)- | 73.5–74.5 | + 18.0° | 1.0 |
| 4-indanyl- | (oil) | + 9.6° | 1.8 |
| m-tolyl- | (oil) | + 13.2° | 1.4 |

EXAMPLE 10

The process described in Example 5 is repeated except that the epoxy-compounds described in Example 9 and either isopropylamine or t-butylamine are used as starting materials. There are thus obtained the (S)—(−)-alkanolamine derivatives described in the following table:

| | | $R^1$—OCH$_2$ . CHOH . CH$_2$NHR$^4$ | | |
|---|---|---|---|---|
| $R^1$ | $R^4$ | M.p.(°C.) | $[\alpha]_D^{21}$ | c (% in solvent) |
| 1-naphthyl- | isopropyl | hydrochloride 189–192 | hydrochloride −22.8° | 1.5% in ethanol |
| p-acetamidophenyl | isopropyl | 129–132 | − 16.0° | 1% in aqueous N-hydrochloric acid |
| o-(N-methyl-carbamoyl-methoxyphenyl)- | t-butyl | hydrochloride 145–147 | hydrochloride −8.5° | 2% in methanol |
| 4-indanyl | isopropyl | hydrochloride 149–150.5 | hydrochloride −8.6° | 1% in methanol |
| m-tolyl | isopropyl | hydrochloride 118–118.5 | hydrochloride −20.2° | 1% in methanol |

EXAMPLE 11 o-Cyanophenol (5.95 g.) is added to a solution of sodium (1.15 g.) in 2-methoxyethanol (20 ml.), the mixture is stirred for 5 minutes, and a solution of 3-t-butoxy-1-toluene-p-sulphonyloxypropan-2-ol (15.1 g.) in 2-methoxyethanol (30 ml.) is added. The mixture is heated under reflux for 90 minutes, cooled and poured into a mixture of ice and water (150 ml.), and the mixture is basified with aqueous 2 N-sodium hydroxide solution and extracted twice with chloroform (100 ml. each time). The combined extracts are washed with water, dried and evaporated to dryness and the residue is chromatographed on a slica gel column using chloroform as eluant. The appropriate fractions of the eluate are evaporated to dryness and there is thus obtained as oily residue 1-o-cyanophenoxy-3-t-butoxypropan-2-ol, the structure of which is confirmed by proton magnetic resonance spectroscopy.

The 3-t-butoxy-1-toluene-p-sulphonyloxypropan-2-ol used as starting material may be obtained as follows:

Isobutylene is bubbled during 3 hours into a solution of 2,3-O-isopropylideneglycerol (12.0 g.) in methylene chloride (175 ml.) containing sulphuric acid (1 ml.) and the mixture is allowed to stand for 18 hours and is then washed three times with 5% aqueous sodium bicarbonate solution (100 ml. each time). The methylene chloride solution is dried and evaporated to dryness and the residue is distilled under reduced pressure. There is thus obtained 1-O-t-butyl-2,3-O-isopropylideneglycerol, b.p. 110°–116° C./50 mm.

A mixture of the above compound (22.5 g.) and 5% aqueous sulphuric acid (100 ml.) is stirred at laboratory temperature for 30 minutes, solid sodium carbonate is added until the pH of the solution is 10 and the mixture is extracted twice with chloroform (100 ml. each time). The combined extracts are washed with water, dried and evaporated to dryness and the residue is distilled under reduced pressure. There is thus obtained 1-O-t-butylglycerol, b.p. 84°–85° C./1.4 mm.

Toluene-p-sulphonyl chloride (14.4 g.) is added to a stirred solution of the above compound (11.2 g.) in pyridine (170 ml.) which is maintained at −15° C., and the mixture is stirred at that temperature until all the chloride has dissolved and then allowed to warm up to 0° C. during 18 hours. The mixture is filtered to remove pyridine hydrochloride and the filtrate is diluted with ethyl acetate (100 ml.) and poured into a cooled mixture of sulphuric acid (66.2 ml.) and water (380 ml.). The ethyl acetate layer is separated and the aqueous acidic layer is extracted three times with ethyl acetate (100 ml. each time). The combined ethyl acetate solutions are washed with brine, dried and evaporated to dryness, and the residue is dissolved in chloroform and chromatographed on a silica gel column using initially chloroform, and then increasing concentrations of ethyl acetate in chloroform, as eluant. The eluate obtained using a 30% v/v solution of ethyl acetate in chloroform is evaporated to dryness and there is thus obtained as oily residue 3-t-butoxy-1-toluene-p-sulphonyloxypropan-2-ol, the structure of which is confirmed by proton magnetic resonance spectroscopy.

EXAMPLE 12

Hydrogen chloride is bubbled during 1 hour into a solution of 1-o-cyanophenoxy-3-t-butoxypropan-2-ol (2.0 g.) in chloroform (50 ml.) and the mixture is allowed to stand for 12 hours and is then evaporated to dryness under reduced pressure. The residue is chromatographed on silica gel plates (Merck 60 $F_{254}$, 2 mm. thick) using ethyl acetate as eluant, and the appropriate bands are scraped from the plates and extracted with methanol. The combined extracts are filtered and evaporated to dryness and there is thus obtained as oily residue 1-o-cyanophenoxypropane-2,3-diol, the structure of which is confirmed by proton magnetic resonance spectroscopy.

This compound is converted into, respectively, 1-o-cyanophenoxy-3-toluene-p-sulphonyloxypropan-2-ol; 1-o-cyanophenoxy-2,3-epoxypropane and 1-o-cyanophenoxy-3-isopropylaminopropan-2-ol by the methods described in, respectively, Examples 3, 4 and 5.

What we claim is:

1. An optically-active compound having the (S)— absolute configuration and having the formula:

R$^1$OCH$_2$.CHOH.CH$_2$OY wherein R$^1$ is phenyl, naphthyl, 5,8-dihydronaphthyl, 5,6,7,8-tetrahydronaphthyl, 5,8-ethano-5,6,7,8-tetrahydronaphthyl, indanyl, indenyl, fluorenyl or anthryl, which is unsubstituted or which bears one, two or three substituents selected from halogen, hydroxy and nitro; alkyl, cycloalkyl, alkenyl, alkynyl, alkoxy, cycloalkoxy, alkenyloxy, alkynyloxy, hydroxyalkyl, hydroxyalkenyl and hydroxyalkoxy, each of up to 6 carbon atoms; aryl, aryloxy, aralkyl, aralkoxy, alkoxyalkyl and alkoxyalkoxy, each of up to 10 carbon atoms; and which may also, where there is an appropriate degree of partial saturation, optionally bear an oxo substituent; and wherein Y is α-aryl-alkyl or tertiary-alkyl.

2. A compound as claimed in claim 1 wherein Y is benzyl.

3. A compound as claimed in claim 1 wherein Y is t-butyl.

4. An optically-active compound as claimed in claim 1 wherein R$^1$ is phenyl, naphthyl, 5,8-dihydronaphthyl, 5,6,7,8-tetrahydronaphthyl, 5,8-ethano-5,6,7,8-tetrahydronaphthyl, indanyl, indenyl, fluorenyl or anthryl which is unsubstituted or which bears one, two or three substituents selected from fluoro, chloro, bromo, iodo, hydroxy, nitro, methyl, ethyl, n-propyl, isopropyl, t-butyl, cyclopropyl, cyclopentyl, allyl, ethynyl, methoxy, ethoxy, isopropoxy, n-butoxy, cyclopentyloxy, allyloxy, propargyloxy, hydroxymethyl, β-hydroxyethyl, 3-hydroxyprop-1-enyl, β-hydroxyethoxy, phenyl, phenoxy, p-tolyloxy, benzyl, benzyloxy, methoxyethyl, methoxyethoxy and ethoxyethoxy; and which may also, where there is an appropriate degree of partial saturation, optionally bear an oxo substituent.

5. An optically-active compound as claimed in claim 1 wherein R$^1$ is 2-tolyl, 3-tolyl, 2,3-dimethylphenyl, 2-chloro-5-methylphenyl, 2-allylphenyl, 2-allyloxyphenyl, 2-cyclopropylphenyl, 2′-cyclopentylphenyl, 1-naphthyl, 5,8-dihydro-1-naphthyl, 5,6,7,8-tetrahydro-5-oxo-1-naphthyl, 5,8-ethano-5,6,7,8-tetrahydro-1-naphthyl, 4-indanyl or 7-indenyl.

6. A compound as claimed in claim 1 wherein Y is benzyl and R$^1$ is 1-naphthyl.

* * * * *